United States Patent [19]

Higuchi et al.

[11] Patent Number: 4,921,703

[45] Date of Patent: May 1, 1990

[54] VERMIN EXTERMINATING ELEMENT AND VERMIN EXTERMINATING METHOD USING IT

[75] Inventors: Toshio Higuchi; Ken Hibino; Rikako Yoshii; Takayuki Hiyori; Yoshinori Miyamoto; Eiichiro Fukusaki; Takeo Matsumura; Yoshiko Hashimoto; Michiko Kikuma; Yuko Sahashi; Takeshi Okada, all of Osaka, Japan

[73] Assignee: Nitto Electric Industrial Co., Ltd., Osaka, Japan

[21] Appl. No.: 99,262

[22] Filed: Sep. 21, 1987

[30] Foreign Application Priority Data

Sep. 19, 1986 [JP] Japan .................. 61-222479
Sep. 19, 1986 [JP] Japan .................. 61-222480
May 14, 1987 [JP] Japan .................. 62-117399

[51] Int. Cl.$^5$ ............................ A61K 39/00
[52] U.S. Cl. ..................... 424/419; 424/409; 424/411; 424/414; 424/486; 424/93; 119/156
[58] Field of Search ............ 424/409, 411, 414, 419, 424/486, 93; 119/156, 159, 160

[56] References Cited

U.S. PATENT DOCUMENTS

| | | | |
|---|---|---|---|
| 3,269,900 | 8/1966 | Rubin ........................ | 424/419 |
| 3,541,203 | 11/1970 | Fogle et al. ................. | 424/93 |
| 3,864,468 | 2/1975 | Hyman et al. ............... | 424/411 |
| 4,223,007 | 9/1980 | Spence et al. .............. | 424/93 |
| 4,237,113 | 12/1980 | Cardarelli ................... | 424/419 |

FOREIGN PATENT DOCUMENTS

| | | |
|---|---|---|
| 0130116 | 6/1983 | France . |
| 50-9868 | 4/1975 | Japan . |
| 53-11316 | 4/1978 | Japan . |
| 55-36313 | 9/1980 | Japan . |
| 57-30452 | 6/1982 | Japan . |
| 60-214878 | 10/1985 | Japan . |
| 857161 | 12/1960 | United Kingdom . |
| 1426101 | 2/1976 | United Kingdom . |
| 82943 | 4/1982 | United Kingdom . |

*Primary Examiner*—Mark L. Bell
*Assistant Examiner*—Karl Group
*Attorney, Agent, or Firm*—Sughrue, Mion, Zinn, Macpeak & Seas

[57] ABSTRACT

A vermin exterminating element comprising a culture carrier having culture medium components containing vermin infectious microorganisms and/or the spores of the vermin infectious microorganisms cultivated therein, and a vermin exterminating method using the same.

31 Claims, 7 Drawing Sheets

FIG. 2a
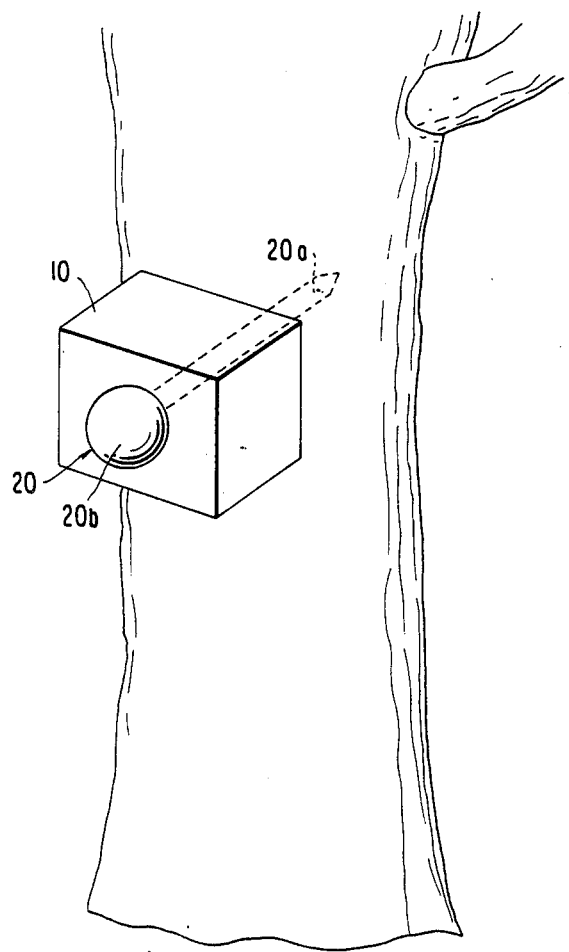
FIG. 2b
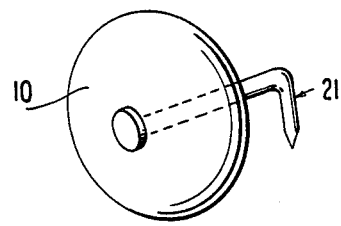
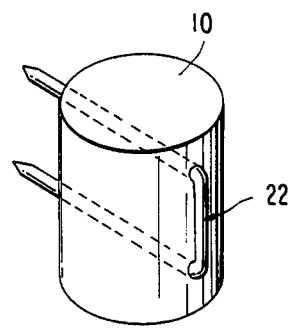
FIG. 2c

FIG. 3a
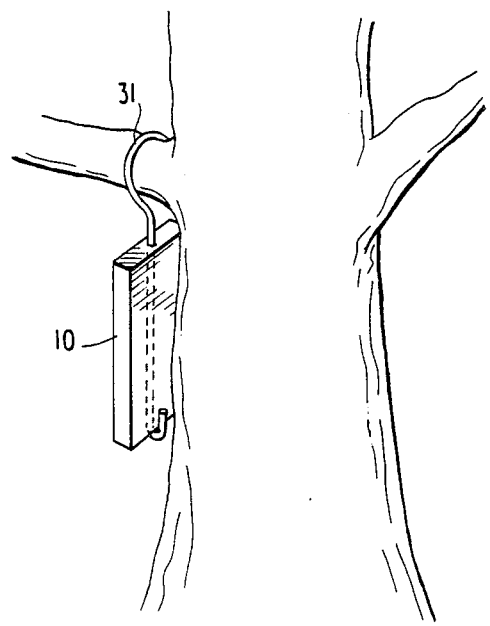
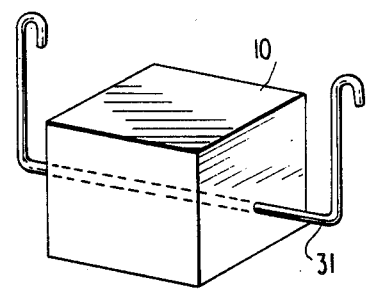
FIG. 3b
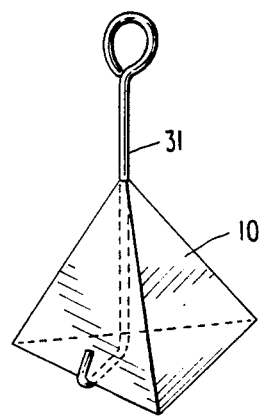
FIG. 3c
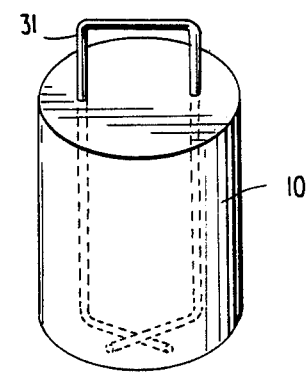
FIG. 3d

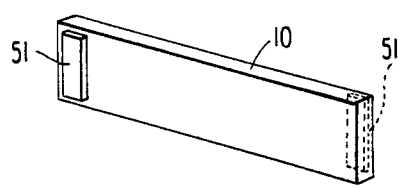
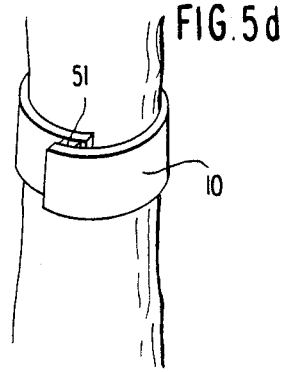
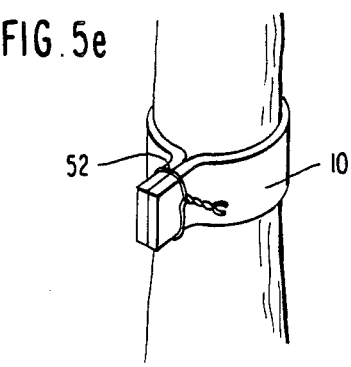
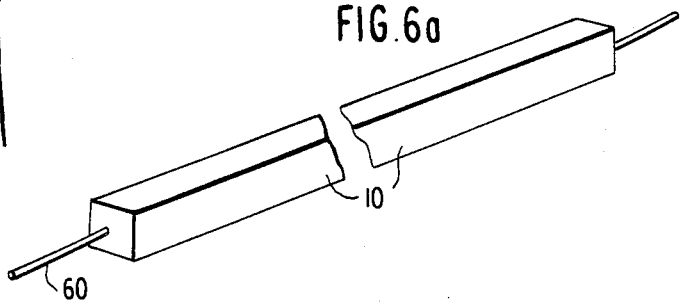
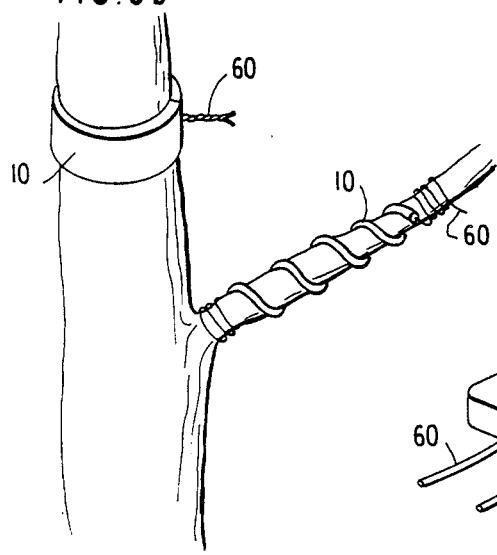
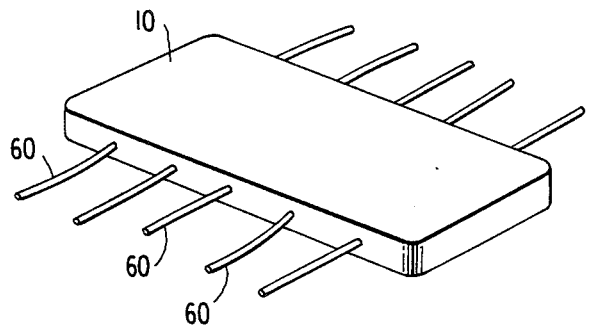

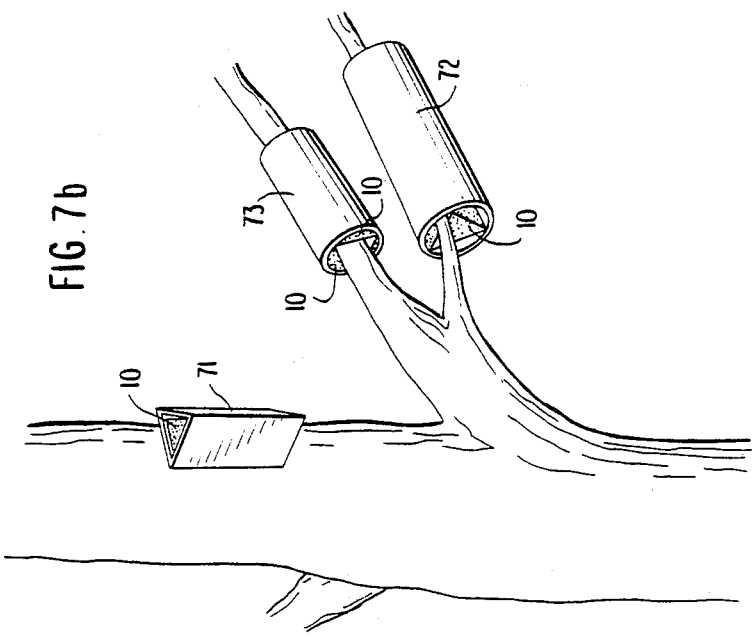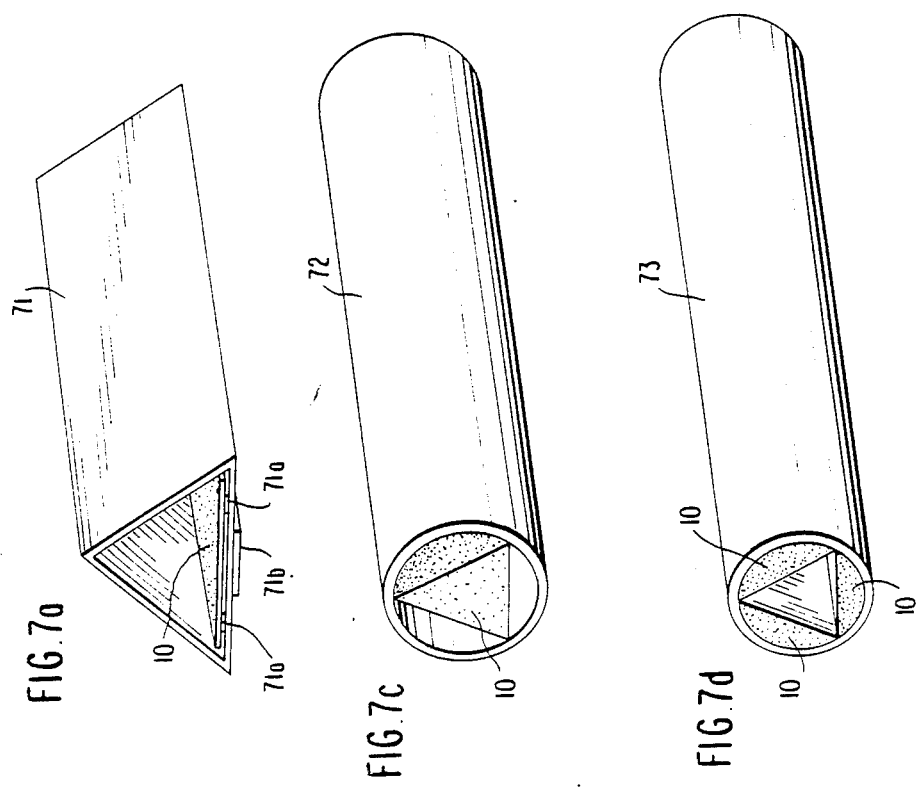

VERMIN EXTERMINATING ELEMENT AND VERMIN EXTERMINATING METHOD USING IT

FIELD OF THE INVENTION

This invention relates to a vermin exterminating element and a vermin exterminating method using the element. More particularly, the invention relates to a vermin exterminating element having excellent insecticidal activity to vermin such as long horned beetles (Cerambycidae), Scarabs, etc., and a vermin exterminating method using the element.

BACKGROUND OF THE INVENTION

Recently, damages of crops by long horned beetles tend to be increased. For example, *Psacothea hilaris* Pascore is parasitic on a mulberry tree and a fig tree, *Anoplophora malasciaca* Thomson is parasitic on a pear tree and an apple tree, and *Acalolepla luxuriosa* Bates is parasitic on an udo (Aralia cordata) to give big damages them. Furthermore, *Monoehamus alternatus* Hope and *Semanotus japonicus* Lacordaire are parasitic on trees. In particular, the damages of mulberry trees are large and spread over a wide range. Long horned beetles lay eggs under bark and the hatched larvae deeply make holes in the xylem to give eaten damages to the trees. The length of the eaten damage hole becomes longer than 60 cm. A mulberry tree having parasitic density loses its physiological function and is withered.

For exterminating long horned beetles, the use of chemical insecticides may be considered. However, since long horned beetles are hole-making vermin, a chemical insecticide is reluctant to reach the larvae in a trunk. Accordingly, it is difficult to effectively exterminate long horned beetles by chemical insecticides.

Also, since mulberry leaves are used for breeding silkworm, the use of a chemical insecticides gives undesirable influences on silkworm. Figs, pears, and apples are foods and hence the use of chemical insecticides for them give injuries to human bodies, animals and plants.

For solving these faults, it has been attempted to use mold fungi (e.g., *Beauveria brongniartii* (*tenella*)) which are natural enemy microorganisms to long horned beetles in place of chemical insecticides. Mold fungi are well parasitic on long horned beetles, in particular, on *Psacothea hilaris* Pascore but do not have phathogenity to silkworms. The extermination of long horned beetles using the mold fungi is performed by cultivating the mold fungi in a wheat bran culture medium and directly dusting the cultured fungi onto trees such as mulberry trees together with the culture medium. Dusting of the cultured fungi is practiced at the adult emergence period of long horned beetles. However, by the method described above, the cultured fungi are in a state near dormant cells since they cannot sufficiently imbibe culture medium components and hence the desired insecticidal effect of the mold fungi cannot be obtained. Furthermore, many of the dusted cultured fungi are absorbed by soil without attaching to trees, which also reduces the insecticidal efficiency. Also, even the fungi attached to trees are in danger of being washed out by natural conditions (rain, wind, etc.). Moreover, dusting of a culture medium containing large amounts of organic substances and high nutriments such as wheat bran, etc., can indiscriminately proliferate natural microorganisms and hence in such a case, there is a danger that a large amount of undesired microorganisms are proliferated to cause secondary microorganism contamination. Such a microorganism contamination reduces the exterminating effect to vermin as well as is in a danger of giving bad influences on human bodies, animals and plants.

SUMMARY OF THE INVENTION

This invention has been made for solving the above-described problems in conventional techniques.

An object of this invention is to provide a vermin exterminating element excellent is insecticidal effect and a vermin exterminating method using the element.

Other object of this invention is to provide a vermin exterminating element giving no injury to men and beasts and a vermin exterminating method using the element.

A still other object of this invention is to provide a vermin exterminating method which can be easily practiced.

This invention has been made based on the inventor's knowledge that a vermin exterminating element having excellent insecticidal effect is obtained by cultivating vermin infectious microorganisms such as mold fungi and/or the spores of the vermin infectious microorganisms in a culture medium containing culture components, the vermin infectious microorganisms and/or the spores of the vermin infectious microorganisms can sufficiently imbibe the culture medium components, whereby a vermin exterminating element giving less leaving or washing out of the vermin exterminating microorganisms and/or the spores of the vermin exterminating microorganisms is obtained, and the insecticidal efficiency is increased by disposing the vermin exterminating element at trees, etc., without accompanying the washing out of the cultivated vermin exterminating microorganisms and/or the spores of the vermin exterminating microorganisms.

It has now been found that the above-described objects have been attained by the invention as set forth below.

That is, the invention is a vermin exterminating element comprising a culture carrier having culture medium components containing vermin infectious microorganisms and/or the spores of vermin infectious microorganism cultured therein.

Other embodiment of this invention is a vermin exterminating method which comprises disposing a vermin exterminating member comprising a culture carrier having culture medium components containing vermin infectious microorganisms and/or the spores of vermin infectious microorganisms cultured therein on trees, etc., to which vermin extermination is applied.

BRIEF DESCRIPTION OF THE DRAWINGS

FIG. 1 to FIG. 8 are views of various embodiments of applying the vermin exterminating elements of this invention to trees.

DETAILED DESCRIPTION OF THE INVENTION

Figure 1A:
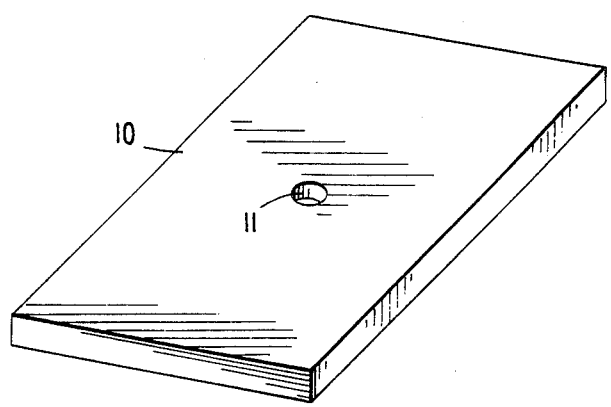
Figure 1B:
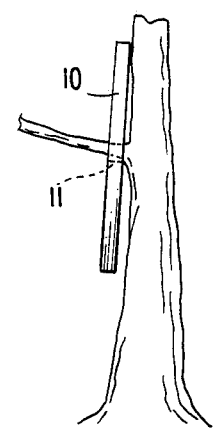
Figure 1C:
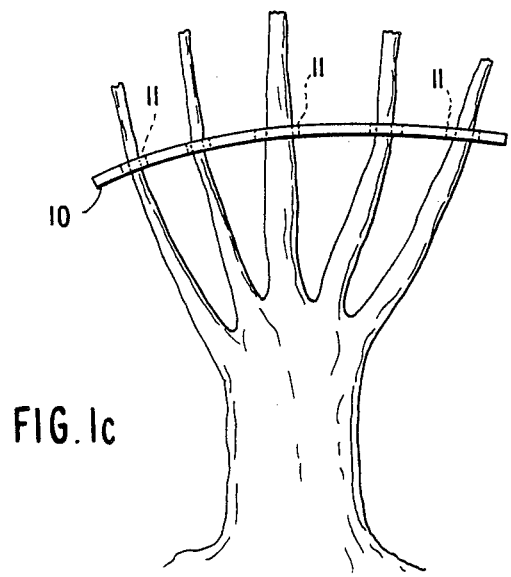

A carrier which can carry culture medium components and can culture vermin infectious microorganisms and/or the spores of vermin infectious microorganisms with the culture components therein can be used as the culture carrier in this invention. Examples of the carrier are boards, cloth pieces, foam matrices, etc., or plastic moldings, board moldings, etc., having attached thereto wheat bran capable of cultivating vermin infectious microorganisms.

As a foam matrix which is used for the culture carrier, there are a polyurethane foam, a polystyrene foam, a polyvinyl chloride foam, a polyethylene foam, and a polyether foam but a polyurethane foam is particularly preferred.

As the vermin infectious microorganisms, there are *Beauveria brongniartii* (*tenella*), *Beauveria bessiana, Metarhizium anisopliae, Verticillium lecanii,* and *Synnematium jonesii.* For the extermination of long horned beetles, *Beauveria brongniartii* (*tenella*) is particularly preferred.

The culture medium components are composed of assimilable carbon sources and nitrogen sources containing inorganic salts and a natural organic substances.

Examples of the carbon source are glucose, saccharose, lactose, maltose, glycerol, starch, and molasses. Examples of nitrogen source are ammonium sulfate, ammonium chloride, and ammonium phosphate. Examples of the inorganic salt are phosphates such as potassium dihydrogenphosphate, etc., magnesium salts such as magnesium sulfate, etc., potassium salts and calcium salts. Also, examples of the natural organic substance are animal tissue extracts and powdered animal tissues, such as a meat extract, a fish meat extract, a chrysalis powder, etc.; vegetable fiber extracts such as a malt extract, corn steep liquor, a soybean oil, etc.; and microorganism cells and extracts thereof, such as dry yeast, a yeast extract, polypeptone, etc.

As the culture medium composed of such culture medium components, a synthetic culture medium such as a Czapek's culture medium, etc., and a natural culture medium such as a chrysalis powder culture medium, an agar culture medium, etc., are used.

In the case of using a foam matrix as a carrier for the culture carrier in this inveniton, the culture carrier is obtained by foaming a foaming composition together with the culture medium components. By employing the aforesaid manner, the culture medium components are incorporated in the inside of the foam matrix and hence the cultivation can be made not only at the surface of the foam but also in the inside thereof, whereby the cultivation of vermin infectious microorganisms and/or the spores of vermin infectious microoranisms is effectively performed. In this case, the vermin infectious microorganisms and/or the spores of vermin infectious microorganisms can sufficiently imbibe the culture medium components existing in the inside of the foam matrix, whereby they do not become dormant cells and the insecticidal effect of the vermin exterminating element is increased. Usually, the culture medium components are mainly physically incorporated in the inside of the foam matrix at foaming of the foaming composition. However, when the culture medium components having an amino group and/or a carboxy group, and the foaming composition has an isocyanate group, the culture medium components cause chemical reaction with the foaming composition at foaming, whereby the culture medium components are carried in the foam matrix by chemical bonding with urea bonds and/or acid amide bonds. Thus, the culture medium components are firmly carried by the foam matrix and at the same time the cultured microorganisms, etc., are incorporated in the foam matrix. Accordingly, the cultured microorganisms or the spores thereof are less separated or flowed out from the foam matrix by natural conditions. Furthermore, in this case, the hydroxy group of the culture medium components generates carbon dioxide gas by causing reaction with the isocyanate group to accelerate the foaming.

A polyurethane foam is obtained by reacting polyether or polyester, an isocyanate compound having two or more isocyanate groups in the molecule, and water or other foaming agent. As the isocyanate compound, polyfunctional isocyanates are usually used and examples thereof are tolylene diisocyanate, diphenylmethane diisocyanate, diphenyl diisocyanate, naphthalene diisocyanate, xylene diisocyanate, butane diisocyanate, and triphenylmethane-4,4',4''-triisocyanate. Polyether or polyester becomes a prepolymer by causing a reaction with the isocyanate compound and by reacting the prepolymer with water, carbon dioxide gas is generated to cause foaming, whereby a polyurethane foam is formed.

A polystyrene foam is formed by adding a foaming agent such as pentane, hexane, heptane, etc., to a polystyrene prepolymer and performing emulsion polymerization in water.

A polyvinyl chloride foam is obtained by a thermal decomposition method or a gas blowing method.

A polyethylene foam is obtained by adding petroleum ether, gaseous freon (Freon 12), etc., to a polyethylene prepolymer and kneading and foaming the mixture by heating.

In the case of any one of the aforesaid foams, by adding the aforesaid culture medium components to the prepolymer of each foam together with a foaming agent, the culture medium components are incorporated in the foam matrix formed. However, in place of employing such a method, a foam matrix is formed using a peptide such as soluble collagen, gelatin, albumin, etc. (the foam matrix is referred to as peptide matrix), and the peptide matrix may be impregnated with the culture medium components. The peptide matrix is formed by reacting an aqueous solution of a peptide and an isocyanate compound having two or more isocyanate groups in the molecule. As the isocyanate compound, the above-described polyfunctional isocyanate is used.

In the aforesaid case, a part of the isocyanate compound reacts with water to generate carbon dioxide gas and other part thereof reacts with the amino group and the carboxy group of the peptide to form a urea bond and an acid amide bond, which results in providing a polyurethane foam having the peptide matrix in the molecule. The polyurethane foam obtained has excellent hydrophilic property and water retentivity according to the properties of the peptide contained in the molecule, and also has excellent naturally collapsing property by a proteolytic enzyme. When the polyurethane foam is impregnated with culture medium components, the culture medium components are firmly carried in the foam matrix.

Alternatively, a peptide may be added to the forming composition while foaming the foaming composition together with the culture medium components, whereby the culture medium components are more fimrly incorporated by both the foam matrix and the peptide matrix.

When the foam matrix is a polyurethane foam, the culture medium components are added to a mixture of the prepolymer (a reaction product of polyether or polyester and an isocyanate compound) and water or other foaming agent for reaction. When the culture medium components are water-soluble, the culture medium components are mixed with the prepolymer as an aqueous solution thereof. When the culture medium components are insoluble in water, the components are dispersed in an aqueous solution of the prepolymer. The amount of water is preferably in the range of from 10 to 100 parts by weight per 100 parts by weight of the prepolymer. If the amount of water is less than 10 parts by weight, the foaming reaction is delayed and hence a foam having desired foam density is not obtained as well as the reaction of the prepolymer and the culture medium components and the incorporation of the culture medium components into the foam matrix become insufficient. On the other hand, if the amount of water is over 100 parts by weight, the reaction of water and prepolymer predominates, whereby the culture medium components are reluctant to be incorporated in the foam matrix.

The proportion of the culture medium components is from 20 to 500 parts by weight, and preferably from 50 to 200 parts by weight, per 100 parts by weight of the prepolymer. If the proportion of the culture medium components is less than 20 parts by weight, the culture medium components are not sufficiently contained in the foam matrix. On the other hand, if the proportion thereof is over 500 parts by weight, the excessive part of the components over 500 parts cannot be carried in the foam matrix.

The foam matrix preferably contains a hydrophilic polymer for increasing water-holding capacity. By the incorporating of a hydrophilic polymer in the foam matrix, the supplement of water to the foam matrix is scarcely necessary. Examples of the hydrophilic polymer are agar, polyvinyl alcohol, and polyacrylamide. Furthermore, by incorporating an attractant for vermin in the culture carrier or by using the attractant together with the vermin exterminating element, the insecticidal effect is more increased.

The culture carrier using such a foam matrix is, after containing a proper amount of water, sterilized in an autoclave (120° C., 1.2 atms), etc., and then inoculated with vermin infectious bacteria. Then, the culture carrier is subjected to cultivation for, for example, about 2 weeks at about 25° C. By the cultivation, the surface of the culture carrier is covered by vermin infectious microorganisms (hyphae) and the spores thereof to provide a desired vermin exterminating element. The spore has higher insecticidal effect to vermin such as long horned beetles than the hypha. The number of spores grown in this case becomes more than $10^5$ per unit area (1 $cm^2$) of the surface of the foam. The number of the spores is usually from $10^5/cm^2$ to $10^7/cm^2$.

The vermin exterminating element thus obtained is mainly used for the extermination of long horned beetles. As an exterminating method, the foam may be dusted onto trees such as mulberry trees, etc., but for increasing the insecticidal effect, it is preferred to dispose the vermin exterminating element obtained on the trunks or branches of a tree, supports of polyvinyl chloride film-made house, etc.

The vermin exterminating element of this invention and the vermin exterminating method using the element can be also applied to Scarabs in addition to long horned beetles. Scarabs give damages not only to a forestry field such as trees, seedings, an afforested area, etc., but also to crops such as strawberries, sweet potatoes, peanuts, etc. If mold fungi are parasitized the imagoes of Scarabs by using the vermin exterminating element of this invention, eggs layed by the imagoes do not hatch even if the imagoes themselves are not killed.

Furthermore, the vermin exterminating element of this invention is effective not only to long horned beetles and Scarabs but also to nematodes (Nematoda) which are parasitic on living plants and give damages thereto. In this case, in place of mold fungi, a bacterium, *Pasteurella pentrance,* which is a natural enemy microorganism to the nematodes can be used.

Various embodiments of using manners of the vermin exterminating element of this invention are explained by referring to the accompanying drawings.

For example, as shown in FIG. 1 (*a*), a culture carrier 10 is shaped into a thin plate and a perforation 11 is formed at the central portion thereof. As shown in FIG. 1 (*b*), a branch of a tree is inserted in the perforation 11 to hang the element on the tree.

Long horned beetles are nocturnal insects and have the habit that the beetles creep about trees and gather at a thick portion of a trunk, etc., at night but they gather at a dark portion such as a shaded portion, etc., in the daytime. Accordingly, if the culture carrier 10 is applied to a trunk of a tree by inserting a branch of the tree into the perforation 11 of the culture carrier 10, a dark portion is formed between the culture carrier 10 and the trunk of the tree. Thus, there is a possibility of gathering long horned beetles at the dark portion and hence the exterminating effect of long horned beetles is more increased.

The perforation 11 formed in the culture carrier 10 may have a size capable of hanging the carrier on a branch of a tree utilizing the perforation but if the thickness of the culture carrier. 10 is relatively increased and the size of the perforation 11 is reduced, the area of the dark portion formed becomes larger, which makes efficient the extermination effect to long horned beetles. The number of the perforation formed in the culture carrier 10 is not limited to one but when a tree has many branches, plural perforations may be formed for hanging the culture carrier 10 on these branches as shown in FIG. 1 (*c*).

Also, in place of hanging the culture carrier using the perforation(s), the culture carrier 10 may be directly fixed to trees, supports of polyvinyl chloride film-made house, etc., a nail-like member 20 as shown in FIG. 2 (*a*). The nail-like member 20 shown in FIG. 2 (*a*) is composed of a metal rod **20*a* having the sharp point and a spherical head portion 20*b* at the other end thereof and the culture carrier 10 is fixed to a tree, etc., by driving the metal rod 20*a* into the cubic culture carrier 10** from the sharp point and also driving the point into the trunk, etc., of the tree.

The form of the nail-like member 20 and the form of the culture carrier 10 are not limited to ones shown in FIG. 2 (*a*) but a spherical culture carrier 10 may be fixed to a tree, etc., by using a nail-like member having the top portion bent at almost right angle as shown in FIG. 2 (*b*). Also, as shown in FIG. 2 (*c*), a culture carrier 10 may be fixed to a tree, etc., using a clamp form nail-like member 22.

A culture carrier 10 may be hung on a tree, etc., using a hanging member 31 as shown in FIG. 3 (*a*) in place of fixing to a tree, etc., using a nail-like member. The hanging member 31 is composed of a wire of a metal such as iron, stainless steel, etc., the member is penetrated into a culture carrier 10 having a form of thin plate almost perpendicularly, the end portion of the metal wire extended over the lower side of the carrier is fixed to the side thereof, and other end portion extended over the upper end thereof is bent for hanging on a branch of a tree, etc. The bent upper portion of the hanging member is hung on the branch of the tree, etc., so that a part of the culture carrier 10 is brought into contact with the trunk of the tree. The material of the hanging member 31 is not limited to metal but a material which is not deteriorated by wind, rain, etc., and can be easily prepared and shaped is preferred.

The hanging member 31 may be a metal wire penetrating almost horizontally through a cubic culture carrier 10 as shown in FIG. 3 (i b). Also, the form of the culture carrier 10 is not limited to a cube but may be a pyramid form as shown in FIG. 3 (c) and further may be a cylindrical form as shown in FIG. 3 (d). In the embodiment shown in FIG. 3 (d), the hanging member 31 is so disposed that the center portion of the metal wire is disposed above the culture carrier and both ends thereof are penetrated through the culture carrier 10 to extend from the low end of the carrier and bent at the end portions and fixed to the lower side of the carrier. The center portion of the metal wire is extended over the upper surface of the culture carrier 10 with a definite gap from the upper surface thereof and is hung on a branch of a tree or a hanging member, etc., fixed to a support of a polyvinyl chloride film-made house by the center portion thereof.

Figure 4A:
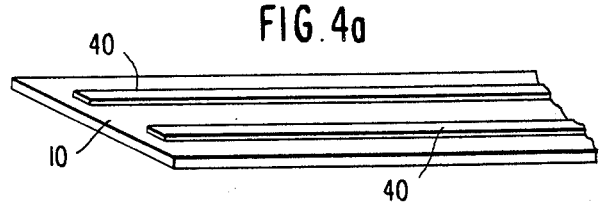
Figure 4B:
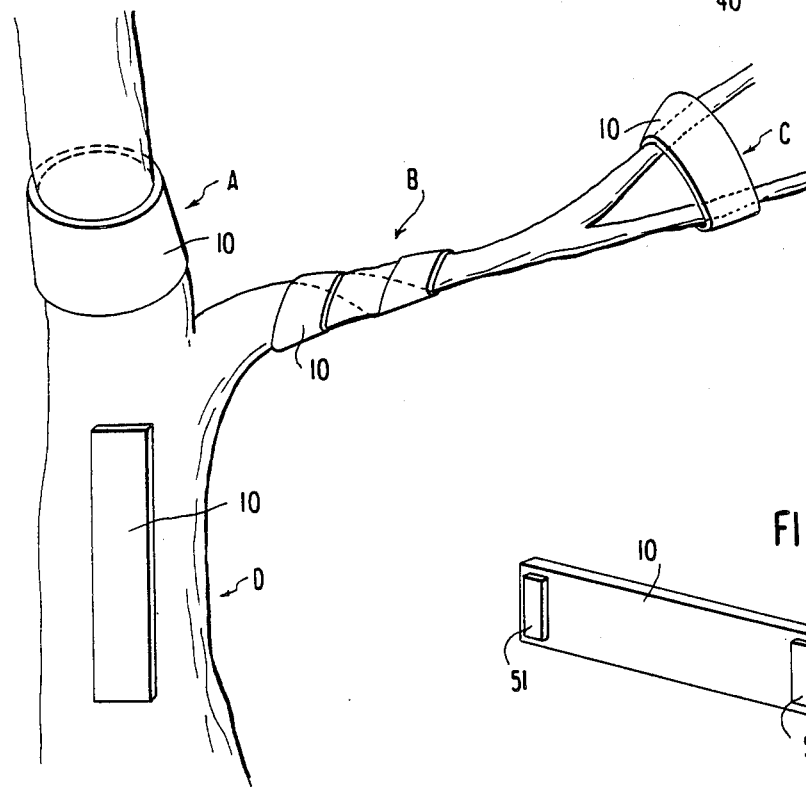

The form of the culture carrier 10 is not limited to a cubic form but may be a band form as shown in FIG. 4 (a). For example, a pair of double faced adhesive tapes 40, 40 are stuck to one surface of such a band form culture carrier 10 and the culture carrier 10 may be stuck to a trunk, a branch, etc., of a tree as shown in FIG. 4 (i b). In place of using double faced adhesive tapes, an adhesive is coated on the surface of the culture carrier 10 and the culture carrier may be stuck to a tree. The culture carrier 10 is stuck to a tree by winding round the tree in a single layer as shown in FIG. 4 A or spirally as shown in FIG. 4 B so that the adhesive surfaces of the both faced adhesive tapes or the adhesive coated surface of the culture carrier is brought into contact with a trunk or branch of the tree. Also, the band form culture carrier 10 is stuck to a tree by winding round two branches of the tree as shown in FIG. 4 C or by sticking to a trunk or a branch of a tree straight along the axis of the trunk or the branch as shown in FIG. 4 D. Since long horned beetles have a habit of creeping on the trunks and branches of a tree as described above, by sticking the band form culture carrier 10 to the trunk or branch of the tree so that the culture carrier covers the trunk or the branch of the tree, the change of the contact of long horned beetles with the culture carrier is increased and the insecticidal effect to long horned beetles is improved. The band form culture carrier may be also stuck to supports of a vinyl chloride film-made house.

Figure 5A:
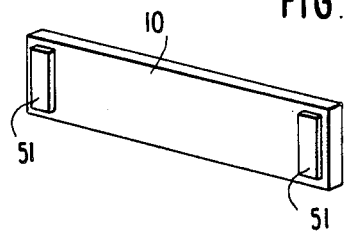
Figure 5B:
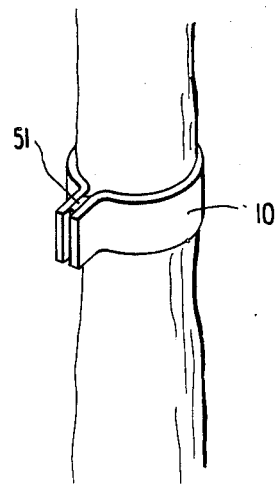
Figure 8A:
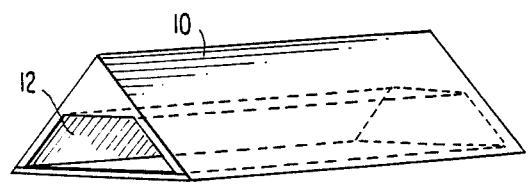
Figure 8B:
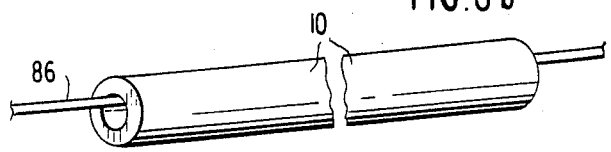
Figure 8D:
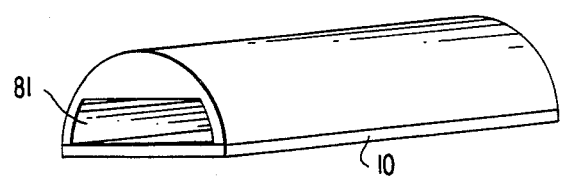
Figure 8C:
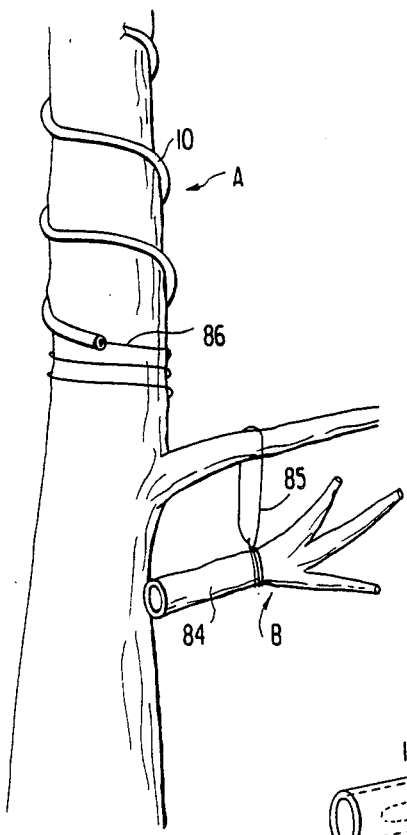
Figure 8E:
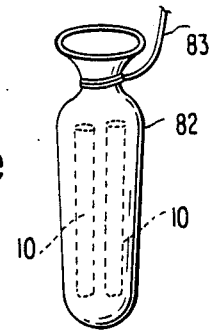
Figure 8F:
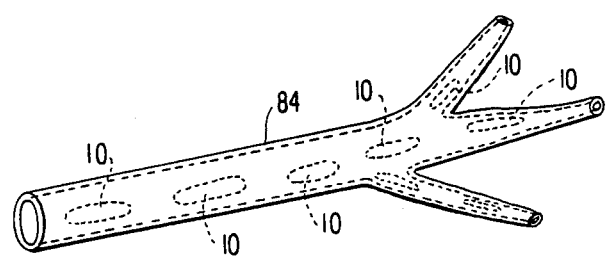

In place of directly sticking the band form culture carrier 10 to a tree, etc., using a double faced adhesive tape or an adhesive as described above, adhesive tapes 51, 51 such as magic tape, etc., are stuck to the end portions of the band form culture carrier 10 in a same surface as shown in FIG. 5 (a), the culture carrier 10 is bound round a trunk or a branch of a tree so that the adhesive tapes 51 are in the inner side, and may be fixed to the tree by sticking the adhesive tapes to each other to fix the end portions of the culture carrier 10 to each other as shown in FIG. 5 (b). Also, adhesive tapes 51, 51 are stuck to the end portions of the band form culture carrier 10 in opposite surfaces as shown in FIG. 5 (c), the culture carrier 10 is bound round a tree so that the adhesive tapes 51, 51 are superposed to each other and the culture carrier may be fixed to the tree by sticking the adhesive tapes to each other as shown in FIG. 5 (d). In addition, for fixing the end portions of the band form culture carrier 10 to each other, a key hook, etc., may be used. Furthermore, for fixing both end portions of the band form culture carrier 10 by binding round a tree, etc., a metal wire or a cord 52 is fixed to one end portion of the culture carrier 10 and the culture carrier 10 may be fixed to a tree by binding round the tree so that the end portions thereof are in contact with other and binding the end portions with the cord 52 as shown in FIG. 5 (e).

When the band form culture carrier 10 is bound round a tree, etc., and both end portions thereof are fixed to each other as described above, the culture carrier 10 is insufficiently brought into contact with the tree over the whole length of the carrier by the existence of unevenness of the surface of the tree to form some gaps between the two members. Thus, since long horned beetles gather in the gaps in the daytime due to the habit as described above, the insecticidal effect is more increased.

Also, for fixing a band form culture carrier 10 by binding round a tree, etc., and fixing the end portions thereof, an embodiment shown in FIG. 6 may be employed. That is, as shown in FIG. 6 (a), a flexible member 60 such as a metal wire or a cord is penetrated through the culture carrier along the axis thereof and both end portions of the flexible member may be extended over the carrier as shown in FIG. 6 (a). Furthermore, the wires or the cords may be fixed to the end portions of the culture carrier 10 without penetrating through the culture carrier.

By employing the above-described manner, the culture carrier 10 is fixed to a tree by binding round the tree in a single layer or spirally and tying the end portions of the wire or cord 60 each other as shown in FIG. 6 (i b). In addition, plural wires or cords 60 may be disposed along the axis of the band form culture carrier 10 and also when the width of the culture carrier 10 is wide, plural wires or cords 60, 60, 60 may be penetrated through the culture carrier 10 in the direction rectangular to the axis thereof as shown in FIG. 6 (c).

In the case of disposing a culture carrier 10 on a tree, etc., a construction that the culture carrier 10 is placed in a tubular case may be employed. In this case, the culture carrier 10 is shaped into tabular form and the tabular culture carrier may be stuck to the inside surface of one side of a triangle-columnar tubular case 71 by an adhesive 71a as shown in FIG. 7 (a). The tubular case 71 containing the culture carrier 10 is equipped to a tree by directly sticking the tubular case 71 to the tree with an adhesive tape 71b stuck to the outside surface of the tubular case or by inserting a branch, etc., of the tree into the tubular case 71 as shown in FIG. 7 (i b).

The form of the tubular case is not limited to triangle-columnar form. Also, the form of the culture carrier 10 placed in the tubular case is not limited to a tabular form. For example, a construction that a triangle-columnar culture carrier 10 is disposed in a cylindrical case 72 as shown in FIG. 7 (c) or a construction that culture carriers 10, 10, 10 are disposed along the inside surface of a cylindrical case 73 so that a triangle-columnar space is formed in the cylindrical case 73 as shown in FIG. 7 (d) may be employed.

It is preferred that the tubular or cylindrical case is formed by a plastic, acryl resin plate, etc., which is not deformed and corroded by wind and rain.

In these cases, the tubular or cylindrical case 71 to 73 containing the culture carrier 10 can be easily attached to a tree, etc., and detached from the tree, etc. In the case of attaching the tubular or cylindrical case 71 to 73 to a tree, the case itself becomes a shelter to form a dark place in the inside thereof and thus long horned beetles gather in the dark place, whereby the insecticidal effect is more increased.

The culture carrier 10 may be so formed that a dark place in the inside thereof for gathering vermin to be exterminated, such as long horned beetles. The dark place is obtained by forming a concaved portion 12 in a triangle-columnar culture carrier 10, said concaved portion having an opening portion at one side of the culture carrier as shown in FIG. 8 (a). When the culture carrier 10 is formed into a tubular form as shown in FIG. 8 (i b), a dark place is formed in the inside space thereof. Such a culture carrier 10 is attached to a tree, a support of a vinyl chloride film-made house, etc., by sticking thereto by an adhesive, etc., or fixing thereto by a wire, etc. When the culture carrier 10 is formed into a tubular form, a wire or cord 86 is inserted into the inside thereof as shown in FIG. 8 (i b) and the culture carrier 10 is fixed to a tree, etc., by spirally winding round the tree as shown in FIG. 8 (c).

Also, in place of forming a dark place in the inside of a culture carrier 10, a construction that a culture carrier 10 is disposed in a dark place may be employed. For example, a semi-cylindrical light-shielding member 81 made of a material having light-shielding property, such as hard paper, plastic, etc., is equipped to a tabular culture carrier 10 and an opening portion is formed at one side thereof as shown in FIG. 8 (d). Thus, one surface of the culture carrier is disposed in the dark and vermin to be exterminated enter the dark portion from the opening. Furthermore, as shown in FIG. 8 (e), tape-form culture carrier 10 are placed in a pouch-form light-shielding member 82, the opening of the pouch-form light-shielding member 82 is narrowed slightly by a wire or cord 83 leaving a definite space, and the member may be hung on a tree, etc., by the wire or cord 83. Moreover, as shown in FIG. 8 (f), a construction that plural block-form culture carriers 10, 10, 10 are disposed in a tubular light-shielding member 84 having branched ends having light-shielding property may be employed. The light-shielding member 84 may be hung on a branch of a tree by a wire or cord 85 with a part of the opening at the end thereof being stuck to the tree as shown in FIG. 8 (c) B.

The light-shielding members 81, 82 and 84 are preferably formed by a material which has a light-shielding property and is not easily damaged by wind and rain, birds, etc., such as plastics, synthetic fibers, metal foils, hard papers, etc.

Then, the invention is explained by referring to the following examples.

EXAMPLE 1

To 1 liter of water was added 40 g of a chrysalis powder, an essence was extracted, and further 20 g of glucose was added to the extract to provide a fundamental culture medium. By reacting 275 g of an aqueous 5% gelatin solution with 1,000 g of an isocyanate compound, Sofranate (trade name, made by Toyo Tire and Rubber Co., Ltd.), a polyurethane foam was obtained.

The polyurethane foam was cut into 30 mm×50 mm×10 mm and was impregnated with the above-described fundamental culture medium. After sterilizing the urethane foam in an autoclave (121° C., 1.2 atms) for 20 minutes, the foam was inoculated with 1 to 5 ml of a culture solution of *Beauveria brongniartii* (*tenella*) and the microorganisms were cultivated for 2 weeks at 25° C.

On the vermin exterminating member thus obtained were walked the imagoes (one male and one female) of *Semanotus japonicus* Lacordaire caught for one minute each. Thereafter, the imagoes were bred at 22° C. while giving honey and water but the male died after 4 days and the female after 7 days. During the breeding period, the female laid eggs, which did not cause hatching.

The dead insects (male and female) of aforesaid *Semanotus japonicus* Lacordaire were surface-treated with alcohol and stored in a plate together with a filter paper impregnated with distilled water at 24° C. As the result thereof, it was confirmed that *Beauveria brongniartii* (*tenella*) locally generated at the join portions of the dead insects.

EXAMPLE 2

The same test as in Example 1 except that *Verticillium lecanii* (separated from dead bodies of *Psacothea hilaris* Pascore) was inoculated in place of *Beauveria brongniartii* (*tenella*) was followed. As the result thereof, the imagoes (male and female) of *Semanotus japonicus* Lacordaire were alive for more than 15 days, the male died after 15 days and the female after 18 days. However, the eggs laid by the female during breeding were covered by mold fungi and did not cause hatching.

When the dead bodies of *Semanotus japonicus* Lacordaire were stored by the same manner as in Example 1, *Verticillium lecanii* generated over the whole surface of the dead body.

EXAMPLE 3

The same experiment as in Example 1 except that the imagoes of *Psacothea hilaris* Pascore were used in place of the imagoes of Semanotus japonicus Lacordaire was followed. As the result, the imagoes died after 2 weeks and the surface of the dead body was covered by *Beauveria brongniartii* (*tenella*) after 4 days since the dead.

EXAMPLE 4

By the same procedure as in Example 1 except that the urethane foam was impregnated with 5 ml of the fundamental culture medium and 5 ml of the culture solution was inoculated, *Beauveria brongniartii* (*tenella*) was cultivated. After cultivating for 2 weeks at 25° C., the number of hyphae was measured and the number was $5.3 \times 10^5$ cells/cm$^2$. The proliferation of the hyphae was lete and the foam itself was almost viewed by eye.

EXAMPLE 5

By following the same procedure as in Example 1 except that the polyurethane foam was impregnated with 10 ml of the fundamental culture medium and 0.014 g of the spores of *Beauveria brongniartii* (*tenella*) was dusted thereto in place of inoculating the culture solution, *Beauveria brongniartii* (*tenella*) was cultivated. When the number of hyphae was measured after cultivating for 2 weeks at 25° C., the number was $6.7 \times 10^5$ cells/cm$^2$. The proliferation of the hyphae was late and the foam itself was almost viewed by eye as in Example 4.

EXAMPLE 6

In 1 liter of the fundamental culture medium as in Example 1 was dissolved 15 g of agar. Then, by following the same procedure as in Example 1 except that the polyurethane foam was impregnated with 1 ml of the aforesaid agar culture medium and 1 ml of the culture solution was inoculated, *Beauveria brongniartii* (*tenella*) was cultivated. When the number of hyphae was measured after cultivating for 2 weeks at 25° C., the number was $3.4 \times 10^7$ cells/cm$^2$. The hyphae were increased to an extent of hiding the polyurethane foam itself. The thickness of the fungi layer was observed on the foam and the surface of the foam was covered by spores.

EXAMPLE 7

In 1 liter of the fundamental culture medium as in Example 1 was dissolved 15 g of agar. Then, by following the same procedure as in Example 1 except that the polyurethane foam was impregnated with 5 ml of the aforesaid agar culture medium and 3 ml of the culture solution was inoculated, *Beauveria brongniartii* (*tenella*) was cultivated. When the number of hyphae was measured after cultivating for 2 weeks at 25° C., the number was $6.0 \times 10^7$ cells/cm$^2$. The hyphae were increased to an extent of hiding the polyurethane foam itself. The thickness of the fungi layer was observed on the foam and the surface of the foam was covered by spores.

EXAMPLE 8

In 1 liter of the fundamental culture medium as in Example 1 was dissolved 15 g of agar. Then, by following the same procedure as in Example 1 except that the polyurethane foam was impregnated with 5 ml of the aforesaid agar culture medium and 0.001 g of the spores of *Beauveria brongniartii* (*tenella*) was dusted thereto, *Beauveria brongniartii* (*tenella*) was cultivated. When the number of hyphae was measured after cultivating for 2 weeks at 25° C., the number was $2.9 \times 10^7$ cells/cm$^2$. The hyphae were increased to an extent of hiding the polyurethane foam itself. The thickness of the fungi layer was observed on the foam and the surface of the foam was covered by the spores.

EXAMPLE 9

After mixing 100 parts by weight of a urethane polymer, 30 parts of a chrysalis powder, 15 parts of glucose, and 11 parts by weight of agar, 30 parts by weight of an aqueous 5% gelatin solution was added thereto to cause foaming and to provide a foam for cultivating microorganisms. After sterilizing the foam in an autoclave (121° C., 1.2 atms) for 20 minutes, the foam was inoculated with 3 ml of a culture solution of *Beauveria brongniartii* (*tenella*) and the cultivation was performed for 2 weeks at 25° C. When the number of the spores was measured after the cultivation, the number was $1.9 \times 10^6$ cells/cm$^2$. The foam itself was partially viewed by eye but the number of the hyphae was about $10^8$ cells/cm$^2$.

EXAMPLE 10

By following the same procedure as in Example 9 except that 2 ml of distilled water was added to the foam before sterilizing the foam, *Beauveria brongniartii* (*tenella*) was cultivated. When the number of the spores was measured after cultivating for 2 weeks at 25° C., the number was $0.7 \times 10^6$ cells/cm$^2$. The foam itself was partially viewed by eye but the number of the hyphae was about $10^8$ cells/cm$^2$.

EXAMPLE 11

By following the same procedure as in Example 9 except that 4 ml of distilled water was added to the foam before sterilizing the foam, *Beauveria brongniartii* (*tenella*) was cultivated. When the number of the spores was measured after cultivating for 2 weeks at 25° C., the number was $0.7 \times 10^6$ cells/cm$^2$. The foam itself was partially viewed by eye but the number of the hyphae was about $10^8$ cells/cm$^2$.

EXAMPLE 12

By following the same procedure as in Example 9 except that 5 ml of distilled water was added to the foam before sterilizing the foam, *Beauveria brongniartii* (*tenella*) was cultivated. When the number of the spores was measured after cultivating for 2 weeks at 25° C., the number was $0.7 \times 10^6$ cells/cm$^2$. The foam itself was partially observed by eye but the number of the hyphae was about $10^8$ cells/cm$^2$.

EXAMPLE 13

By following the same procedure as in Example 9 except that 10 ml of distilled water was added to the foam before sterilizing the foam, *Beauveria brongniartii* (*tenella*) was cultivated. When the number of the spores was measured after cultivating for 2 weeks at 25° C., the number was $0.7 \times 10^6$ cells/cm$^2$. The spores were formed over the whole surface of the foam. The number of the hyphae was about $10^8$ cells/cm$^2$.

EXAMPLE 14

By following the same procedure as in Example 9 except that 12 ml of distilled water was added to the foam before sterilizing the foam, *Beauveria brongniartii* (*tenella*) was cultivated. When the number of the spores was measured after cultivating for 2 weeks at 25° C., the number was $1.4 \times 10^6$ cells/cm$^2$. The spores were formed over the whole surface of the foam. The number of the hyphae was about $10^8$ cells/cm$^2$.

EXAMPLE 15

By following the same procedure as in Example 9 except that 18 ml of distilled water was added to the foam before sterilizing the foam, *Beauveria brongniartii* (*tenella*) was cultivated. When the number of the spores was measured after cultivating for 2 weeks at 25° C., the number was $1.1 \times 10^6$ cells/cm$^2$. In other sample, the number of the spores was $1.3 \times 10^6$ cells/cm$^2$ or $1.8 \times 10^6$ cells/cm$^2$. The spores were formed over the whole surface of the foam. The number of the hyphae was about $10^8$ cells/cm$^2$.

EXAMPLE 16

The polyurethane foam obtained in Example 9 was cut into 50 mm $\times$ 500 mm $\times$ 10 mm and magic tapes were fixed to both ends of the foam. The tape-form urethane foam was impregnated with a proper amount of water and after sterilizing the foam, the foam was inoculated with about 50 ml of a culture solution of *Beauveria brongniartii* (*tenella*) to provide a vermin exterminating element. When the foam was bound round a trunk of a tree and allowed to stand, the release of the hyphae was not occurred even after one week. The spores were also formed.

COMPARISON EXAMPLE 1

When in the test of Example 1, the imagoes of *Semanotus japonicus* Lacordaire were not walked on the vermin exterminating element, they could alive for 15 days.

COMPARISON EXAMPLE 2

When in the test of Example 3, the imagoes of *Psacothea hilaris* Pascore were not walked on the vermin exterminating element, they could aline for more than 30 days.

As is clear from the aforesaid examples and the comparison examples, the vermin exterminating elements using a foam as the carrier for the culture carrier are excellent in insecticidal effect to long horned beetles. Since vermin infectious microorganisms such as molds are cultivated in the foam matrix, the culture efficiency is high. Also, when the vermin exterminating element is allowed to stand on a trunk of a tree, etc., the hyphae are not separated or flowed out.

The vermin exterminating element of this invention is high in culture efficiency and excellent in insecticidal effect since vermin infectious microorganisms and/or the spores thereof are cultivated in the inside of the culture carrier. The vermin exterminating element of this invention is particularly high in insecticidal effect to long horned beetles. In the case of using a foam matrix for the culture carrier, the cultured microorganisms and/or the spores thereof are formed carried in the foam matrix and hence are not released or flown out by natural conditions. Furthermore, since in this invention insects are killed by using microorganisms and/or the spores thereof, they give less damages to men and beasts as compared with chemical insecticides. In the vermin exterminating method of this invention, the vermin exterminating element may be disposed on a trunk or branch of a tree and hence the microorganisms are not absorbed by soil and are effectively used for exterminating vermin. The culture carrier in this invention is disposed on a tree, etc., by hanging on, sticking to, binding round, or fixing to the tree and hence the vermin exterminating method of this invention can be easily practiced. Accordingly, the vermin exterminating element and the vermin exterminating method of this invention can be effectively utilized for the extermination of long horned beetles and Scarabs.

While the invention has been described in detail and with reference to specific embodiments thereof, it will be apparent to one skilled in the art that various changes and modifications can be made therein without departing from the spirit and scope thereof.

What is claimed is:

1. A vermin exterminating element comprising a culture carrier having culture medium components containing entomogenous fungi and/or the spores of the entomogenous fungi cultivated therein, wherein said culture carrier is a foam matrix selected from the group consisting of a polyurethane foam, a polystyrene foam, a polyvinyl chloride foam, polyethylene foam, and a polyether foam.

2. The vermin exterminating element as claimed in claim 1, wherein the entomogenous fungi are selected from the group consisting of *Beauveria brongniartii (tenella)*, *Beauveria bassiana*, *Metarhizium anisopliae*, *Verticillium lecanii*, and *Synnematium jonesii*.

3. The vermin exterminating element as claimed in claim 1, wherein the culture medium is a foam matrix impregnated with the culture medium components.

4. The vermin exterminating element as claimed in claim 1, wherein the foam matrix is a polyurethane foam.

5. The vermin exterminating element as claimed in claim 1, wherein the foam matrix is produced by the reaction of a peptide and an isocyante compound.

6. The vermin exterminating element as claimed in claim 3, wherein the foam matrix is produced by the reaction of a peptide and an isocyanate compound.

7. The vermin exterminating element as claimed in claim 1, wherein the foam matrix contains a hydrophilic polymer for improving water-holding capacity.

8. The vermin exterminating element as claimed in claim 3, wherein the foam matrix contains a hydrophilic polymer for improving water-holding capacity.

9. The vermin exterminating element as claimed in claim 1, wherein the vermin infectious microorganisms are for exterminating long horned beetles and/or Scarabs by infecting the long horned beetles and/or Scarabs with them.

10. A vermin exterminating method, which comprises disposing a vermin exterminating element comprising a culture carrier having culture medium components containing entomogenous fungi and/or the spores of the entomogenous fungi cultivated therein on a tree, crops or poles, to which a vermin extermination is applied, wherein said culture carrier is a foam matrix selected from the group consisting of a polyurethane foam, a polystyrene foam, a polyvinyl chloride foam, a polyethylene foam, and a polyether foam.

11. The vermin exterminating method as claimed in claim 10, wherein the entomogenous fungi are selected from the group consisting of *Beauveria brongniartii (tenella)*, Beauveria bassiana, Metarhizium anisopliae, Verticillium lecanii, and Synnematium jonesii.

12. The vermin exterminating method as claimed in claim 10, wherein the culture carrier is a foam matrix impregnated with the culture medium components.

13. The vermin exterminating method as claimed in claim 10, wherein the foam matrix is a polyurethane foam.

14. The vermin exterminating method as claimed in claim 12, wherein the foam matrix is a polyurethane foam.

15. The vermin exterminating method as claimed in claim 12, wherein the culture carrier is produced by the reaction of peptide and an isocyanate compound.

16. The vermin exterminating method as claimed in claim 12, wherein the culture carrier is produced by the reaction of peptide and an isocyanate compound.

17. The vermin exterminating method as claimed in claim 10, wherein the foam matrix contains a hydrophilic polymer for improving the water-holding capacity.

18. The vermin exterminating method as claimed in claim 12, wherein the foam matrix contains a hydrophilic polymer for improving the water-holding capacity.

19. The vermin exterminating method as claimed in claim 10, wherein the vermin infectious microorganisms are for exterminating long horned beetles and/or Scarabs by infecting the long horned beetles and/or Scarabs with them.

20. The vermin exterminating method as claimed in claim 10, wherein the culture medium has perforation(s)

through which a trunk or branch of a tree to which vermin extermination is applied can be penetrated.

21. The vermin exterminating method as claimed in claim 10, wherein the culture carrier is fixed to a tree, crops or poles, by driving a nail-like member through the culture carrier into the tree.

22. The vermin exterminating method as claimed in claim 10, wherein the culture carrier is hung on a tree, crops or poles, by a hanging means.

23. The vermin exterminating method as claimed in claim 10, wherein the culture carrier is a band-form culture carrier.

24. The vermin exterminating method as claimed in claim 23, wherein the culture carrier is stuck to a tree, crops or poles.

25. The vermin exterminating method as claimed in claim 23, wherein the culture carrier is bound round a tree, crops or poles.

26. The vermin exterminating method as claimed in claim 10, wherein the culture carrier has a flexible wire or cord penetrated therethrough and is fixed to a tree, crops or poles, by the wire or cord.

27. The vermin exterminating method as claimed in claim 10, wherein the culture carrier is placed in a pouch-form case.

28. The vermin exterminating method as claimed in claim 27, wherein the pouch-form case is stuck to a tree, crops or poles.

29. The vermin exterminating method as claimed in claim 27, wherein the pouch-form case is hung to a tree, crops or poles, through the case.

30. The vermin exterminating method as claimed in claim 10, wherein the culture carrier has a dark place in the inside thereof.

31. The vermin exterminating method as claimed in claim 10, wherein the culture carrier is placed in a dark place.

* * * * *